(12) United States Patent
Hunter et al.

(10) Patent No.: US 8,619,370 B2
(45) Date of Patent: Dec. 31, 2013

(54) OPTICAL COMBINER FOR COMBINING MULTIPLE LASER BEAMS IN A FLOW CYTOMETER

(75) Inventors: Susan Hunter, Fort Collins, CO (US); Daniel N. Fox, Fort Collins, CO (US); Tidhar Sadeh, Fort Collins, CO (US); Matthias J. G. Ottenberg, Holmen, WI (US); Kevin P. Raley, Windsor, CO (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 240 days.

(21) Appl. No.: 13/100,261

(22) Filed: May 3, 2011

(65) Prior Publication Data

US 2012/0105967 A1  May 3, 2012

Related U.S. Application Data

(60) Provisional application No. 61/330,849, filed on May 3, 2010.

(51) Int. Cl.
*G02B 27/14* (2006.01)

(52) U.S. Cl.
USPC .......................... 359/634; 359/629; 359/900

(58) Field of Classification Search
USPC .......................... 359/634, 629, 900
See application file for complete search history.

(56) References Cited

U.S. PATENT DOCUMENTS

| | | |
|---|---|---|
| 4,076,420 A | 2/1978 | DeMaeyer et al. |
| 2002/0122167 A1 | 9/2002 | Riley et al. |
| 2005/0174572 A1 | 8/2005 | Czarnek |
| 2007/0197886 A1 | 8/2007 | Naganuma et al. |
| 2007/0247997 A1 | 10/2007 | Yanagawa et al. |
| 2008/0245779 A1 | 10/2008 | Nomaru et al. |
| 2009/0010589 A1 | 1/2009 | Robertson |
| 2009/0122311 A1 | 5/2009 | Kanda |

OTHER PUBLICATIONS

International Search Report, mailed Sep. 27, 2011, in PCT Application Serial No. PCT/US2011/035075.

*Primary Examiner* — Jack Dinh
(74) *Attorney, Agent, or Firm* — William W. Cochran; Cochran Freund & Young LLC (57) ABSTRACT

Disclosed is an optical combiner for combining multiple laser beams in a flow cytometer. A dichroic beam combiner is used to combine a second laser beam with a first laser beam so that the two beams are collinear. A beam size adjuster is utilized to adjust the size and convergence/divergence of the second laser beam so that both laser beams focus in a vertical direction at the same location on a stream in the flow cytometer. A cylindrical lens with a vertically oriented axis in the focusable beam shaping optics can also be adjusted to adjust the location of the focus point of the two beams in the horizontal direction. Alignment is maintained with the opto-mechanical adjustments made on one laser beam relative to the other laser beam path. Additional beams can also be added to the optical path.

13 Claims, 7 Drawing Sheets

OPTICAL COMBINER FOR COMBINING MULTIPLE LASER BEAMS IN A FLOW CYTOMETER

CROSS-REFERENCE TO RELATED APPLICATION

This application claims benefit of and priority to U.S. Provisional Patent Application Ser. No. 61/330,849, filed May 3, 2010, by Susan Hunter, Daniel N. Fox, Tidhar Sadeh, Matthias J. G. Ottenberg and Kevin P. Raley, entitled "Optical Combiner for Combining Multiple Laser Beams in a Flow Cytometer," the entire contents of which are specifically incorporated herein by reference for all that they disclose and teach.

BACKGROUND

Flow cytometry requires optical sources to be focused on a small stream of fluid for the purpose of illuminating particles, which may be cells, chromosomes, viruses, etc. in the stream of fluid. The particles are then sorted based upon the emissions of fluorochromes that have been used to dye or stain the particles. The processes of illuminating the particles and subsequently sorting these particles are very complex. Optical focusing systems to focus multiple laser beams, as well as optical imaging systems to collect the responses of the particles to the laser excitation, must be deployed in a confined area. As such, the optical systems employed by flow cytometers must be compact and provide a high degree of functionality.

SUMMARY

An embodiment of the present invention may therefore comprise a method of combining laser beams in a flow cytometer comprising: providing a first laser beam; focusing the first laser beam with focusable beam shaping optics, having a first cylindrical lens oriented in a first direction and a second cylindrical lens oriented in a second direction that is substantially orthogonal to the first direction, to form a first elliptically shaped focal point, that is focused at a predetermined location that is substantially centrally located on a fluid stream of the flow cytometer; providing a second laser beam; adjusting beam size and divergence of the second laser beam using a beam size adjuster to form an adjusted second laser beam which forms a second elliptically shaped focal point at substantially the predetermined location, the second elliptically shaped focal point having a size and shape that is substantially the same as the first elliptically shaped focal point; combining the first laser beam and the adjusted second laser beam substantially concentrically using a beam combiner so that the first laser beam and the adjusted second laser beam are applied to the focusable beam shaping optics in a substantially concentric combined beam.

An embodiment of the present invention may further comprise an optical combiner for combining laser beams in a flow cytometer that illuminates particles in a fluid stream comprising: a first laser beam having a first frequency, a first beam size and a first divergence; a second laser beam having a second frequency, which is different from the first frequency, a second beam size and a second divergence; a beam adjuster that adjusts the second beam size and the second divergence of the second laser beam to form an adjusted second laser beam; an optical beam combiner that substantially concentrically combines the first laser beam and the second laser beam to form a substantially concentric combined beam; focusable beam shaping optics aligned with the substantially concentric combined beam, having a first cylindrical lens oriented in a substantially vertical lens axis direction and a second cylindrical lens oriented in a substantially horizontal lens axis direction, the second cylindrical lens disposed to focus the first laser beam and the second adjusted laser beam in a vertical direction on a flow stream of the flow cytometer, the first cylindrical lens adjustably disposed to focus the first laser beam and the adjusted second laser beam in a horizontal direction so that the adjusted second laser beam forms a second elliptically shaped focal point on the fluid stream that is substantially aligned with a first elliptically shaped focal point formed by the first laser beam on the fluid stream.

An embodiment of the present invention may further comprise an optical combiner for combining laser beams in a flow cytometer that illuminates particles in a fluid stream comprising: a first laser beam having a first frequency, a first beam size and a first divergence; a second laser beam having a second frequency, which is different from the first frequency, a second beam size and a second divergence; an optical beam combiner that substantially concentrically combines the first laser beam and the second laser beam to form a substantially concentric combined beam; focusable beam shaping optics aligned with the substantially concentric combined beam, having a first cylindrical lens axis oriented in a substantially vertical direction and a second cylindrical lens axis oriented in a substantially horizontal direction, the second cylindrical lens focusing the first laser beam and the second laser beam in a vertical direction, the first cylindrical lens focusing the first laser beam and the second laser beam in a horizontal direction; a beam adjuster aligned with the second laser beam upstream from the focusable beam shaping optics, that adjusts the second beam size and the second divergence of the second laser beam so that the focusable beam shaping optics focus both the first laser beam and the second laser beam in an elliptically shaped focal point on the fluid stream.

DETAILED DESCRIPTION OF THE EMBODIMENTS

Figure 1:
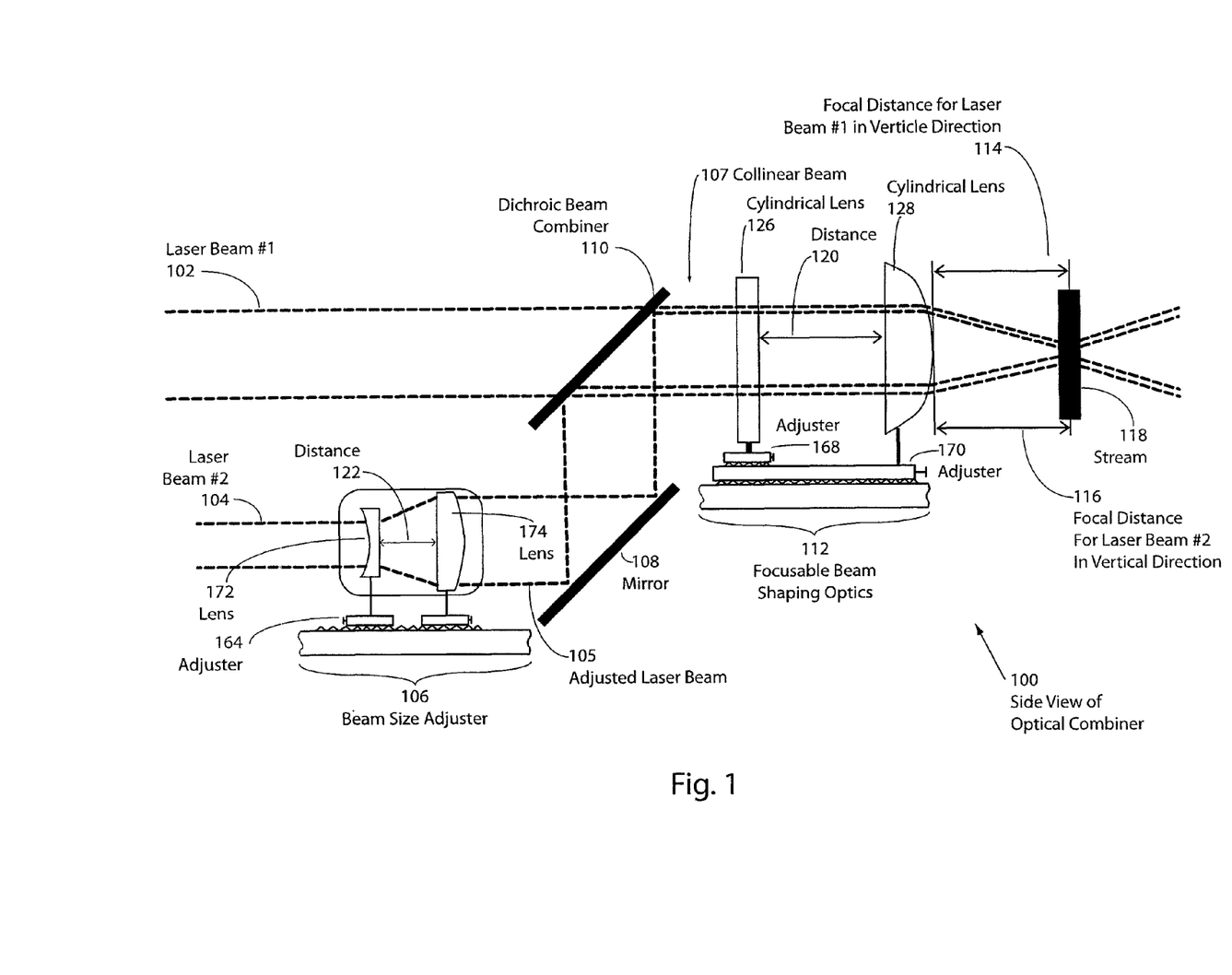
FIG. 1 is a side view of an embodiment of an optical combiner.

FIG. 1 is a side view of an embodiment of an optical combiner 100. As shown in FIG. 1, the optical combiner 100 combines laser beam 102 and laser beam 104 into a combined, substantially collinear beam which is focused on a stream 118 of a flow cytometer. In the past, individual lasers have been focused to a spot or focal point on the stream in a flow cytometer, such as stream 118. The reason for focusing the beam is to increase the power density of the optical energy of the laser at the point at which the laser beam impinges upon the fluid stream. A typical laser beam emitted by a laser can have a cross-sectional diameter that can range from 0.3 millimeters to 2.5 millimeters. Typical optics are capable of focusing the beam to approximately 20 microns in the vertical direction and approximately 60 microns in the horizontal direction.

As instrumentation has progressed, it has been desirable to add additional lasers at different wavelengths to detect different markers. Various fluorochromes are used to match various markers. The excitation band of a particular fluorochrome may require a particular wavelength laser. Since it is desirable to detect multiple markers and utilize Boolean logic to classify and sort a particle, additional lasers may be required to excite the excitation bands of these additional fluorochromes. Hence, the more lasers that can be used in a flow cytometer, the more applications that can be run on the flow cytometer, and the flow cytometer becomes more flexible in its operation. The optical focusing systems used to focus the laser beam on a stream, such as stream 118, as well as the imaging systems that image the scattered or emitted light occupy a large amount of space in a very confined area. For example, the imaging system may require one or more objectives be placed near the stream and occupy a significant space adjacent the stream.

To reduce the amount of space occupied by laser systems, prior art devices have combined beams in fiber optic cables, which require significantly less room. One of the problems encountered with the use of fiber optic cables is that they are expensive and do not transmit UV radiation with high efficiency. Many of the lasers that are used to excite the excitation bands of various fluorochromes are UV lasers. Hence, the application of fiber optic cable in flow cytometers is limited. Even if lasers that have frequencies below the UV range are combined in a fiber optic cable, the use of tandem or conjugate dyes is restricted. In that regard, optical fiber cannot be used with lasers that have wavelengths less than approximately 400 nanometers, and restricted power is available through fiber optical cables at wavelengths from 400 nanometers to 435 nanometers.

Other techniques that have been used to employ more lasers have included movable mirrors that select one laser from two or more laser beams for a single path. However, different wavelengths focus at different focal lengths through the same optics. Moreover, differences in beam diameters of various lasers as well as differences in divergence/convergence of the beam cause additional problems by causing the focal points to occur at substantially different locations. Additionally, movable mirrors only allow use of a single laser at any one time. Faced with these problems, the use of movable mirrors is difficult.

FIG. 1 illustrates an embodiment, which is capable of delivering two or more laser beams as collinear laser beams, or co-propagating laser beams, to the same location on a fluid stream through the same optical path. As illustrated in FIG. 1, a first laser beam 102 is propagated along an optical path through a dichroic beam combiner 110. The first laser beam 102 has a predetermined beam size. A second laser beam 104, as illustrated in FIG. 1, has a different beam size. The second laser beam 104 is applied to beam size adjuster 106 that adjusts the size and divergence/convergence of the second laser beam 104. This is accomplished using standard beam size adjusters, such as disclosed in Optical Design Fundamentals for Infrared Systems, Second Edition, Vol. TT48, SPIE Press, ISBN 9780819440518, which is specifically incorporated herein by reference for all that it discloses and teaches. The beam size adjuster 106, illustrated in FIG. 1, functions as a beam expander and utilizes a negative focal length lens 172 and a positive focal length lens 174. The focal lengths of the negative and positive lenses 172 and 174 can be changed to vary the magnification of the beam adjuster such that the adjusted laser beam 105 will have the desired vertical spot size at focus. In some cases the second laser beam 104 may be the proper size for its particular frequency, so that the second laser beam 104 will have the proper vertical spot size. As such, the size of the beam does not have to be adjusted by the beam size adjuster 106. In another embodiment, a variable magnification beam adjuster could be utilized instead of a fixed magnification system. The distance 122 is generally set according to the beam adjuster equations and can also be adjusted to vary the beam convergence/divergence of the second laser beam 104 to create an adjusted laser beam 105 with the desired size and convergence/divergence. The convergence/divergence may need to be altered to create a beam that can be combined with the first laser beam 102 such that both vertical focal distances 114 and 116 occur at substantially the same location. Adjustment of the lens is accomplished by operating adjuster 164. The adjusted laser beam 105 is reflected from mirror 108 onto dichroic beam combiner 110. In other embodiments, the beam combining may be performed with beam splitters, polarized filters, prisms, or other optical devices. The location of the second laser beam 104 as well as the angles of mirror 108 and dichroic beam combiner 110 cause the adjusted laser beam 105 to be collinearly combined with the first laser beam 102. In other words, if the first laser beam 102 is a circular beam and the second laser beam 104 is a circular beam the two laser beams share a common axis. The collinear beams are then projected onto focusable beam shaping optics 112. Focusable beam shaping optics 112 includes a cylindrical lens 126 with a vertically oriented axis and a cylindrical lens 128 with a horizontally oriented axis. As used herein, the term vertical is used as meaning the direction in which the stream of the flow cytometer flows, while horizontal means the direction that is generally orthogonal to the direction of flow of stream 118, since stream 118 normally flows in a vertical direction. Cylindrical lens 126 and cylindrical lens 128 are separated by a distance 120. Cylindrical lens 126 can be adjusted using adjuster 168 to change the distance 120 between cylindrical lens 126 and cylindrical lens 128 and, consequently, the distance of cylindrical lens 126 from stream 118. Cylindrical lens 126 has a cylindrical axis that is substantially aligned in the vertical direction. Cylindrical lens 128 has a cylindrical axis that is substantially aligned in the horizontal direction. By changing the distance 120 between the cylindrical lens 126 to the stream 118, the focus of the collinear beams can be adjusted in the horizontal direction. Adjuster 170 adjusts the position of the entire focusable beam shaping optics 112. In other words, adjuster 170 adjusts the position of the entire focusable beam shaping optics 112 with respect to stream 118. Cylindrical lens 128 focuses the collinear beam 107 in the vertical direction using adjuster 170. In other words, by using adjuster 170, the position of the focal point of collinear beam 107 in a vertical direction can be adjusted by lateral adjustment of adjuster 170, i.e., in a left-right direction as illustrated in FIG. 1, to bring the vertically focused beam to coincide with stream 118.

Since the second laser beam 104 has a frequency that is different from the first laser beam 102, the index of refraction for the second laser beam 104 is different than the index of refraction for the first laser beam 102 in the focusable beam shaping optics 112. In order to obtain maximum power delivered to the stream 118, both the first laser beam 102 and the second laser beam 104 should be focused in a vertical direction at the same lateral location, which is the location of the stream 118. In that regard, beam size adjuster 106 adjusts the size and the convergence/divergence of the second laser beam 104 so that the focal distance 116 for the second laser beam in the vertical direction is substantially the same as the focal distance 114 for the first laser beam 102, in the vertical direction. During setup, the adjuster 170 is adjusted while the first laser beam 102 is on and the second laser beam 104 is off. In that manner, the first laser beam 102 can be adjusted so that the first laser beam 102 focuses on the stream 118 at focal distance 114. The first laser beam 102 is then turned off and the second laser beam 104 is turned on. The beam size adjuster 106 is adjusted using adjuster 164 to vary the divergence/convergence of the second laser beam 104, so that the second laser beam 104 has a focal distance 116 that is approximately the same as focal distance 114 in the vertical direction. In this manner, the second laser beam 104 also focuses on the stream 118 in the vertical direction.

Figure 2:
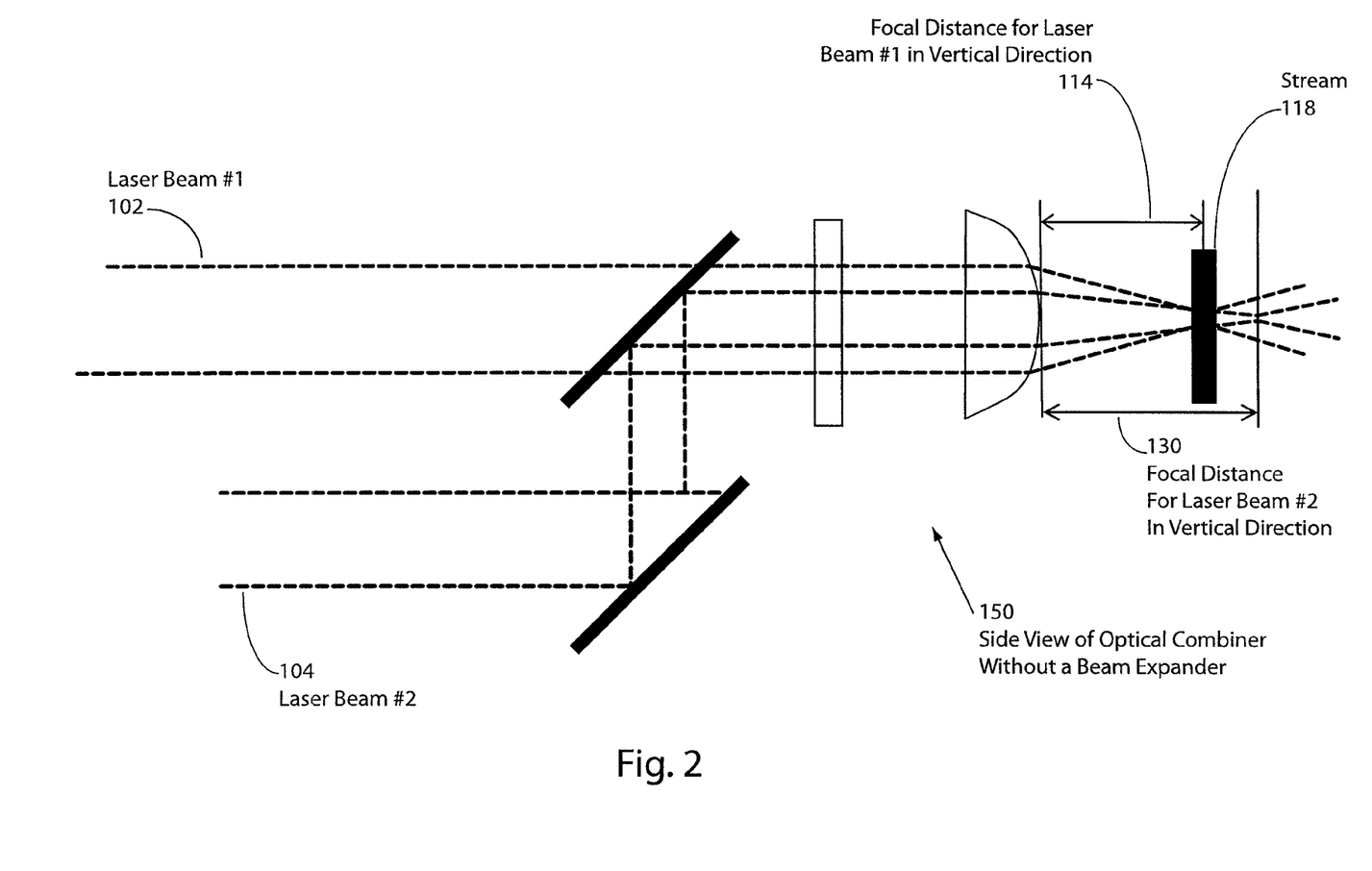
FIG. 2 is a side view of an embodiment of an optical combiner without a beam expander.

FIG. 2 is a side view 150 of an optical combiner without a beam size adjuster, such as beam size adjuster 106 of FIG. 1. As shown in FIG. 2, the first laser beam 102 has a focal distance 114 that focuses the first laser beam 102 in a vertical direction on stream 118. Since the second laser beam 104 does not use a beam size adjuster, such as beam size adjuster 106 of FIG. 1, the second laser beam 104 has a focal distance 130 in the vertical direction. Hence, the second laser beam 104 does not focus, in the vertical direction, on the stream 118, and an optimal amount of power is not delivered to the stream 118 by the second laser beam 104.

Figure 3:
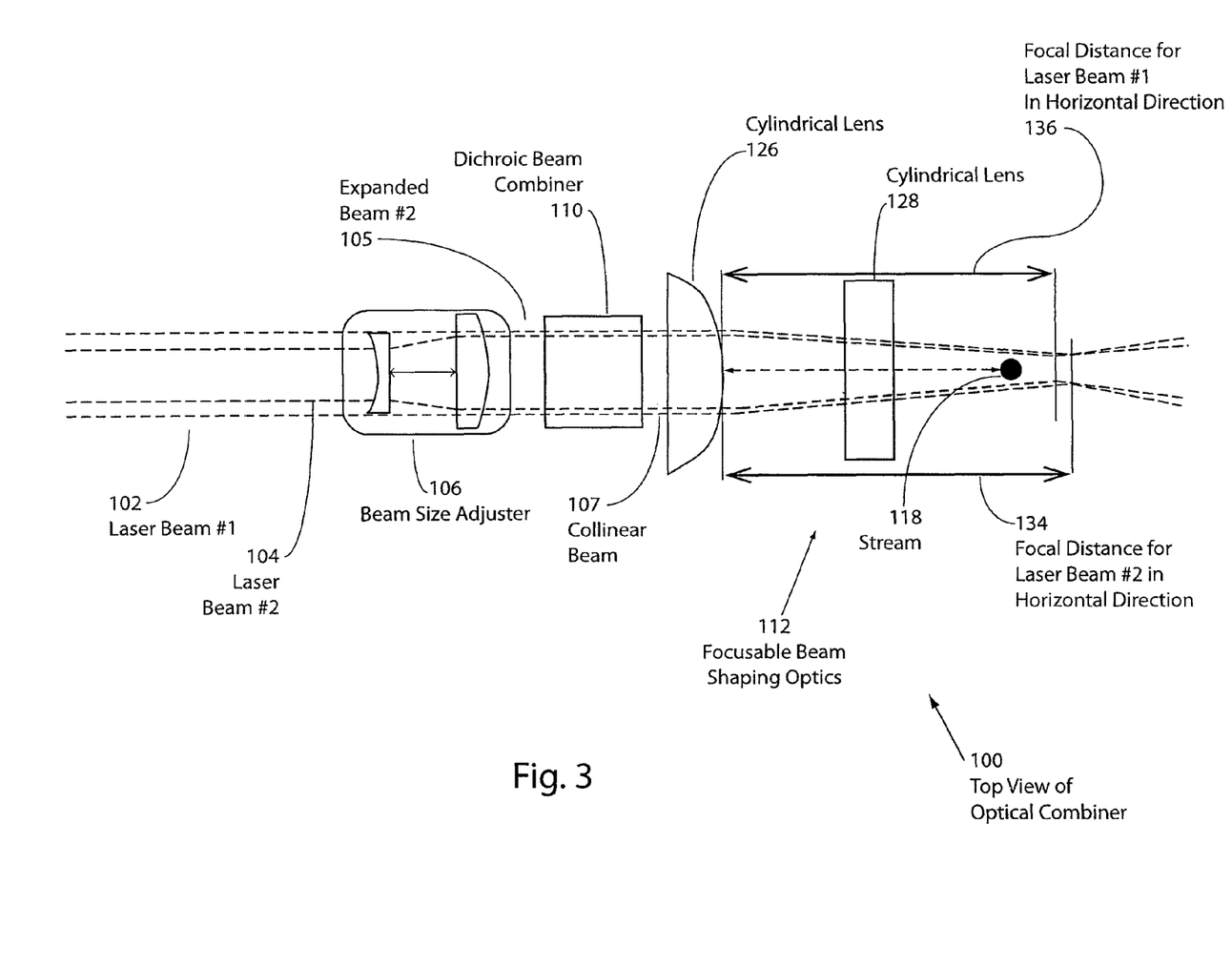
FIG. 3 is a top view of the embodiment of FIG. 1 of the optical combiner.

FIG. 3 is a top view of the optical combiner 100 of FIG. 1. As illustrated in FIG. 3, the first laser beam 102 has a different diameter than the second laser beam 104. The second laser beam 104 is transmitted through the beam adjuster 106, which expands the second laser beam 104 to produce an expanded second laser beam 105. Dichroic beam combiner 110 combines the two beams so that the two beams are collinear. The collinear beam 107 is then transmitted to the focusable beam shaping optics 112. While cylindrical lens 128 substantially controls the focus in the vertical direction, as discussed above, cylindrical lens 126 substantially controls the focus of the collinear beam 107 in the horizontal direction. As shown in FIG. 3, the first laser beam 102 has a focal distance 136 in the horizontal direction. The second laser beam 104 has a focal distance 134 in the horizontal direction, which is different from the focal distance 136 of the first laser beam in the horizontal direction. Adjustment of lens 126, using adjuster 168 (FIG. 1), changes the position of the horizontal focal distance 136 and the horizontal focal distance 134 relative to the position of stream 118.

Figure 4:
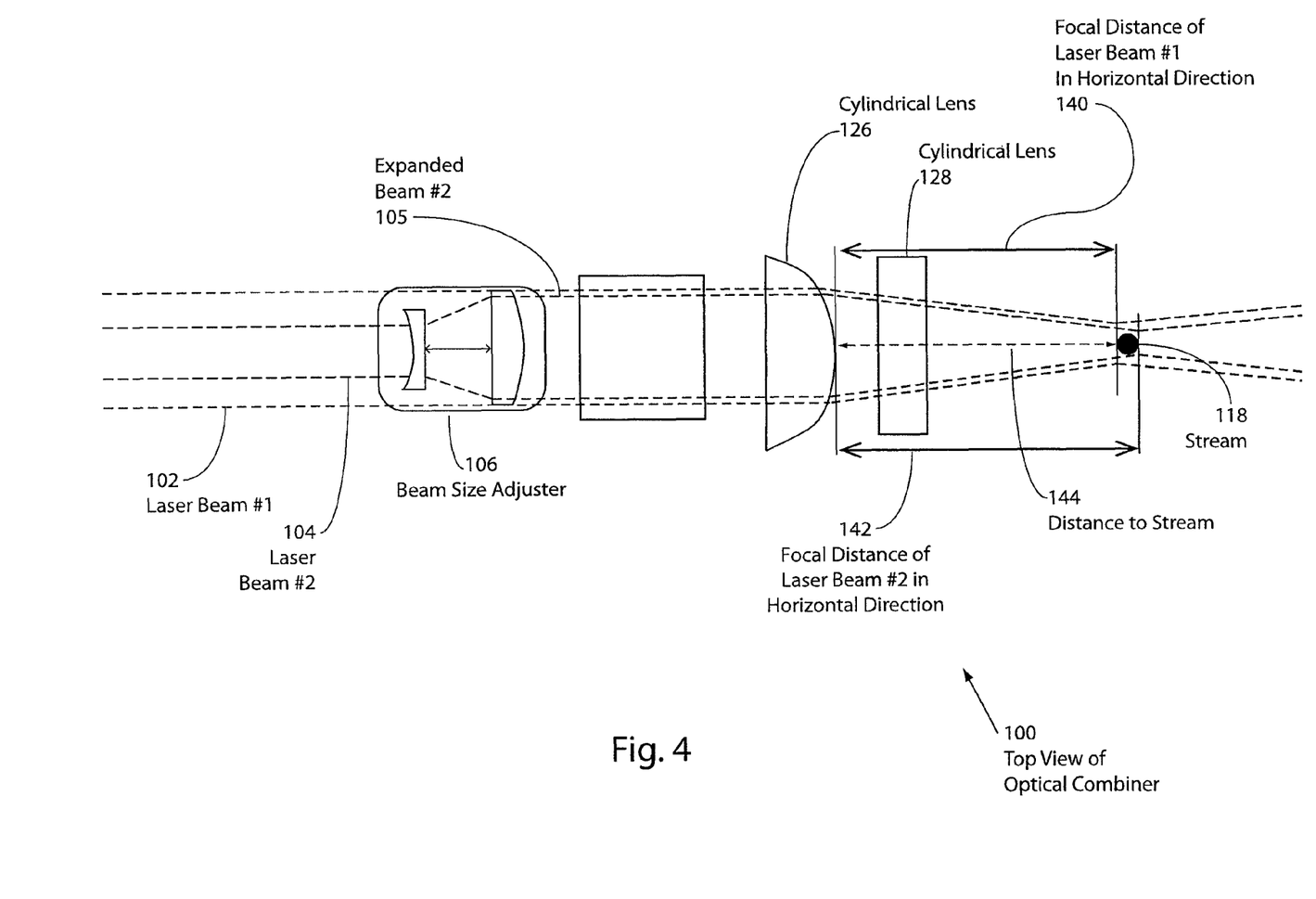
FIG. 4 is another top view of the embodiment of the optical combiner of FIG. 1.
Figure 5:
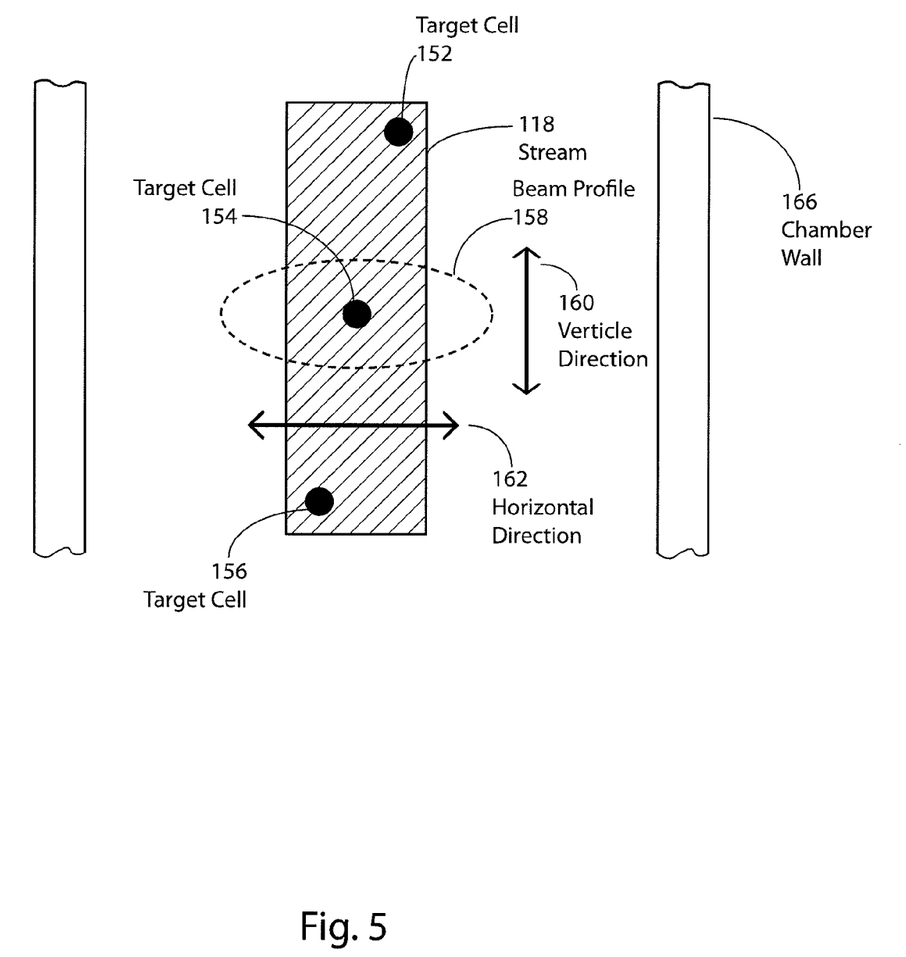
FIG. 5 is a side view illustrating the flow stream and target cells.

FIG. 4 is also a top view of the optical combiner 100, illustrated in FIGS. 1 and 3. As illustrated in FIG. 4, the cylindrical lens 126 has been moved in a lateral direction, to the left, using adjuster 168 (FIG. 1). This causes both the focal distance 140 of the first laser beam 102 and the focal distance 142 of the second laser beam to be adjusted relative to the location of the stream 118. As shown in FIG. 4, cylindrical lens 126 focuses both of the laser beams 102, 104 in a wider area in the horizontal direction, which may typically be from two to four times wider than the focus in the vertical direction. In that regard, cylindrical lens 126 causes the laser beams 102, 104 to have an elliptical beam profile 158, as illustrated in FIG. 5. The purpose of having the concentric beams concentrated in an elliptical profile 158 is to create a wider profile in the horizontal direction across the beam. This allows the stream, as well as the particles in the stream, to move in the horizontal direction without drastically negatively affecting the response of the flow cytometer by increasing the coefficient of variation of the collected data. Since cylindrical lens 126 has an axis in the vertical direction, cylindrical lens 126 can be moved with very little change to the focal position in the vertical direction. The focus of the two laser beams 102, 104 in the vertical direction, as shown in FIG. 1, does not necessarily align the two focal points in the horizontal direction. FIG. 3 illustrates that the focus of the two laser beams 102, 104 in the vertical direction results in focal distances 134, 136 that do not focus either of the beams on the target in the horizontal direction. By moving the cylindrical lens 126, the focal distances 140, 142 can be optimized for best performance, i.e., the highest power and stability. In that regard, cylindrical lens 126 may be focused until the distance 144 to the stream is between the focal distances 140, 142, as shown in FIG. 4. The cylindrical lens 126 may also be focused at other distances if a power or stability gain is achieved.

The diameter of the focal point is given by Equation 1.

$$D_s = (4\lambda/\pi)(F/D) \quad \text{(Equation 1)}$$

where: $\lambda$=wavelength
F=focal length of lens
D=diameter of laser beam entering lens To match the spot diameters for the laser beams 102, 104, it is simply a matter of scaling the diameters of the second laser beam 104 according to Equation 2.

$$\text{Diameter}_{Beam\ 2} = \text{Diameter}_{Beam\ 1} * (\text{wavelength}_{Beam\ 2}/\text{wavelength}_{Beam\ 1}) \quad \text{(Equation 2)}$$

The depth of focus is determined by Equation 3.

$$DOF = (8\lambda/\pi)(F/D)^2 \quad \text{(Equation 3)}$$

where: $\lambda$=wavelength
F=focal length of lens
D=diameter of laser beam entering lens As can be seen from Equation 3, the depth of focus (DOF) increases with the square of the focal length. Hence, in a system in which a spot width is three times the spot height, the depth of focus in the horizontal direction is nine times the depth of focus in the vertical direction. Accordingly, there is a large tolerance with regard to setting the position of cylindrical lens 126. For example, a laser at 488 nanometers with a cross-sectional diameter of 1 millimeter will focus to a spot size of 25 microns in the vertical direction and 75 microns in the horizontal direction. The depth of field in the vertical direction is 2 millimeters while the depth of field in the horizontal direction is greater than 17 millimeters.

FIG. 5 is a side view of a stream 118 in a chamber having chamber walls 166 in a flow cytometer. Beam profile 158 is a typical beam profile that shows the relative size of the beam profile 158 with regard to the stream 118. A plurality of target cells 152, 154, 156 are disposed in different locations in the stream 118. Hence, it is advantageous to have a beam profile 158 that is capable of covering the targets 152-156 in the horizontal direction 162 as the fluid stream moves in the vertical direction 160.

Figure 6:
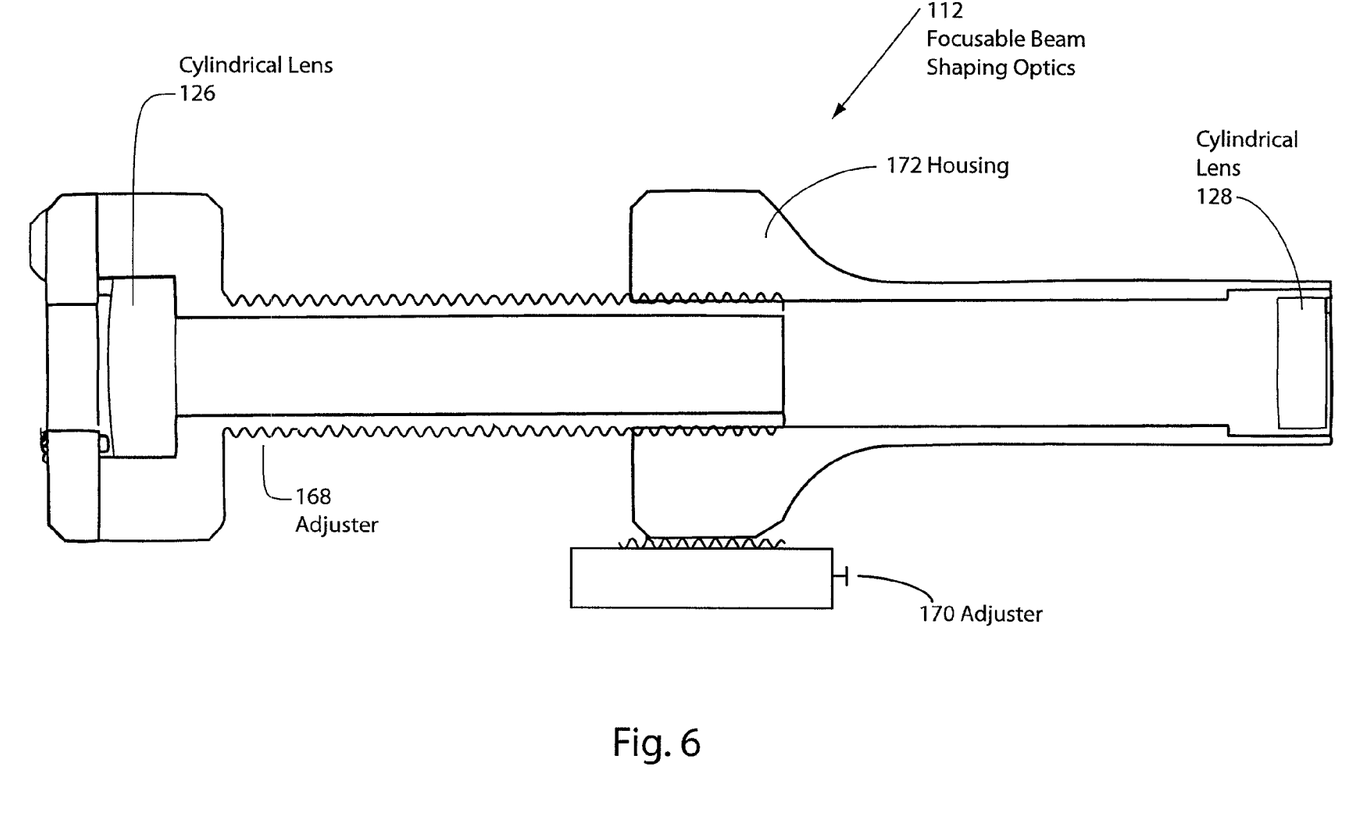
FIG. 6 is a cross-sectional view of an embodiment of focusable beam shaping optics.

FIG. 6 is a cutaway view of one embodiment of focusable beam shaping optics 112. As shown in FIG. 6, cylindrical lens 128 is disposed at one end of the focusable beam shaping optics 112. Cylindrical lens 126 is disposed at the other end of the focusable beam shaping optics 112 and can be adjusted by adjuster 168, which is threaded into housing 172. Cylindrical lenses such as that used for the focusable beam shaping optics 112 can be purchased from Thor Labs at 435 Route 206 North, Newton, N.J. 07860 USA.

Figure 7:
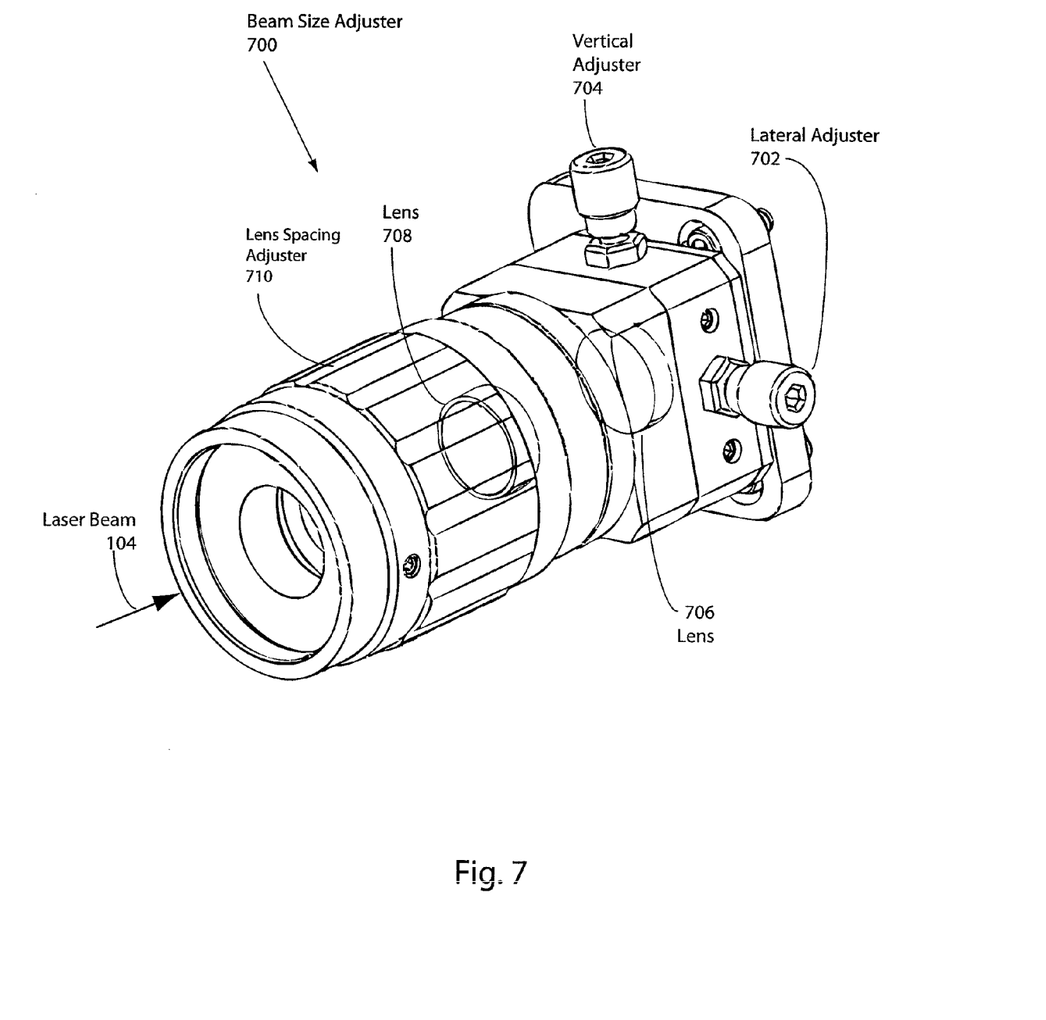
FIG. 7 is a perspective view of an alternative embodiment of a beam size adjuster.

FIG. 7 is a cutaway view of one embodiment of the beam size adjuster 700, which is an alternative embodiment of the beam size adjuster 168, illustrated in FIG. 1. As illustrated in FIG. 7, lens 706 and lens 708 are mounted in the beam size adjuster 700. Lens spacing adjuster 710 adjusts the length between lens 708 and lens 706. Lateral adjuster 702 is coupled to lens 706. Lateral adjuster 702 adjusts lens 706 in a lateral direction by rotating lateral adjuster 702. The lateral adjustment is in the direction along the axis of the lateral adjuster 702. Vertical adjuster 704 is also coupled to the lens 706. Vertical adjuster 704 adjusts the vertical position of lens 706 in a vertical direction. The vertical direction is the direction along the axis of vertical adjuster 704, which is substantially orthogonal to the lateral direction in which the lens 706 is adjusted by lateral adjuster 702. The use of lateral adjuster 702 and vertical adjuster 704 allows laser beam 104 to be accurately adjusted in the beam size adjuster 700. Negative and positive focal length lenses such as those used for the beam size adjuster 106 can be purchased from Thor Labs at 435 Route 206 North, Newton, N.J. 07860 USA.

Hence, the disclosed embodiments take advantage of several unique requirements for the beam shaping optics in flow cytometers and require only a few optical additions and mechanical adjustments in the single laser path. As illustrated in the embodiment of FIG. 1, the beam shaping optics 112 is focusable so that beams 102, 104 can both be focused in both the vertical and horizontal direction. In addition, the beam size adjuster 106 functions to adjust the size and convergence/divergence of laser beam 104 so that cylindrical lens 128 can focus the second laser beam 104 on the stream 118 in the vertical direction with a high degree of precision, such that the focal distance 116 of the second laser beam in the vertical direction is the same as the focal distance 114 for the first laser beam in the vertical direction, even though the second laser beam 104 has a different frequency than the first laser beam 102. The combination of the negative focal length lens 172 and positive focal length lens 174, in the beam size adjuster 106, allows for adjustment of the beam size. The distance 122 between these elements allows adjustment of the convergence/divergence of laser beam 104. Since the second laser beam 104 is adjusted by the beam size adjuster 106 to achieve a vertical focal position that substantially coincides with the focal position of first laser beam 102, additional laser beams can be added to the optical path and combined with the first laser beam 102 using additional dichroic beam combiners. The laser beam diameter of each additional laser beam can be changed to best create the desired final focal spot size according to Equations 1 and 2, and the separation of the lens in the beam size adjuster 106 can be used as a fine adjustment for the beam convergence/divergence in order to tune the position of the focal spot in the vertical direction. Translation of the cylindrical lens 126 in a lateral direction to adjust the focus point in the horizontal direction is performed to provide the best compromise between the horizontal focal position of the first laser beam 102 and the second laser beam 104. Since the two laser beams have a very long depth of focus in the horizontal direction, there is very little degradation, and possibly improvement in the focus of the two beams in the horizontal direction. Additionally, these adjustments need not be performed on a daily basis. Once a particular set of lasers is manufactured and aligned to be collinear, adjustment of the optical elements may not be required.

However, in the case in which the system experiences changes such that the substantially concentric vertical focal points separate due to environmental changes, changes during warm-up cycle, aging, etc., additional adjustments can be added to the system to substantially realign the vertical focal points of the various laser paths to be concentric once again.

FIG. 7 shows the additional adjust knob 704 added to the second lens of the beam expander to allow for small changes in the vertical position of the focal point at the stream. In addition, the adjuster 710 is used in an identical manner as described previously to bring the vertical focal point of the second laser to a substantially similar focal position at the stream as laser beam #1. FIG. 7 shows the third and final adjustment knob 702 that is required to make small changes in the horizontal focal position to bring the second laser beam to a be concentric with the first laser beam. There are other ways to achieve the adjustment of the vertical and horizontal position of the focus, including placing the X-Y translation stage on the first lens of the beam expander or putting a tip-tilt adjustment on the mount holding the mirror 108 or the dichroic 110.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of combining laser beams in a flow cytometer comprising:
   providing a first laser beam;
   focusing said first laser beam with focusable beam shaping optics, having a first cylindrical lens oriented in a first direction and a second cylindrical lens oriented in a second direction that is substantially orthogonal to said first direction, to form a first elliptically shaped focal point, that is focused at a predetermined location that is substantially centrally located on a fluid stream of said flow cytometer;
   providing a second laser beam;
   adjusting beam size and divergence of said second laser beam using a beam size adjuster comprising a negative focal length lens and a positive focal length lens to form a substantially collimated second laser beam which forms a second elliptically shaped focal point at substantially said predetermined location, said second elliptically shaped focal point having a size and shape that is substantially the same as said first elliptically shaped focal point;
   combining said first laser beam and said substantially collimated second laser beam substantially concentrically using a beam combiner so that said first laser beam and said substantially collimated second laser beam are applied to said focusable beam shaping optics in a substantially concentric collimated beam.

2. The method of claim 1 where said process of combining said first laser beam and said substantially collimated second laser beam is performed with a dichroic beam combining mirror.

3. The method of claim 2 further comprising:
   adjusting said focusable beam shaping optics by moving said first cylindrical lens with respect to said fluid stream to adjust a horizontal focal point of said first laser beam and said substantially collimated second laser beam.

4. The method of claim 3 wherein said process of adjusting beam size and divergence of said second laser beam further comprises:
   adjusting beam size and divergence of said second laser beam using said beam adjuster so that said substantially collimated second laser beam is focused in a vertical direction by said second cylindrical lens at substantially said predetermined location.

5. The method of claim 4 wherein said process of adjusting beam size and divergence of said second laser beam comprises:
   adjusting a distance between a first lens and a second lens in said beam adjuster.

6. The method of claim 4 wherein said process of adjusting beam size and divergence further comprises:
   adjusting said negative focal length lens in said beam adjuster in a first direction that is substantially orthogonal to said second laser beam;
   adjusting said positive focal length lens in said beam adjuster in a second direction that is substantially orthogonal to said second laser beam.

7. An optical combiner for combining laser beams in a flow cytometer that illuminates particles in a fluid stream comprising:
   a first laser beam having a first frequency, a first beam size and a first divergence;
   a second laser beam having a second frequency, which is different from said first frequency, a second beam size, which is different from said first beam size, and a second divergence;
   a beam adjuster comprising a negative focal length lens and a positive focal length lens that adjusts said second beam size and said second divergence of said second laser beam to form a substantially collimated second laser beam;
   an optical beam combiner that substantially concentrically combines said first laser beam and said second laser beam to form a substantially concentric collimated beam;
   focusable beam shaping optics aligned with said substantially concentric collimated beam, having a first cylindrical lens oriented in a substantially vertical lens axis direction and a second cylindrical lens oriented in a substantially horizontal lens axis direction, said second cylindrical lens disposed to focus said first laser beam and said second substantially collimated laser beam in a vertical direction on a flow stream of said flow cytometer, said first cylindrical lens adjustably disposed to focus said first laser beam and said substantially collimated second laser beam in a horizontal direction so that said substantially collimated second laser beam forms a second elliptically shaped focal point on said fluid stream that is substantially aligned with a first elliptically shaped focal point formed by said first laser beam on said fluid stream.

8. The optical combiner of claim 7 where said optical beam combiner is a dichroic beam combining mirror.

9. The optical combiner of claim 7 further comprising:
   an adjustment device coupled to said first cylindrical lens that allows said first cylindrical lens to move with respect to said fluid stream to focus said first laser beam and said substantially collimated second laser beam in a horizontal direction.

10. The optical combiner of claim 7 wherein said beam adjuster further comprises:
    a first adjuster that adjusts said negative focal length lens in said beam adjuster in a first direction that is substantially orthogonal to said second substantially collimated laser beam;
    a second adjuster that adjusts said positive focal length lens in said beam adjuster in a second direction that is substantially orthogonal to said second laser beam and said second direction.

11. An optical combiner for combining laser beams in a flow cytometer that illuminates particles in a fluid stream comprising:
    a first laser beam having a first frequency, a first beam size and a first divergence;
    a second laser beam having a second frequency, which is different from said first frequency, a second beam size, which is different from said first beam size, and a second divergence;
    an optical beam combiner that substantially concentrically combines said first laser beam and said second laser beam to form a substantially concentric combined beam;
    focusable beam shaping optics aligned with said substantially concentric combined beam, having a first cylindrical lens oriented in a substantially vertical lens axis direction and a second cylindrical lens oriented in a substantially horizontal lens axis direction, said second cylindrical lens focusing said first laser beam and said second laser beam in a substantially vertical direction, said first cylindrical lens focusing said first laser beam and said second laser beam in a substantially horizontal direction;
    a beam adjuster aligned with said second laser beam upstream from said focusable beam shaping optics, that adjusts said second beam size and said second divergence of said second laser beam using a negative focal length lens in combination with a positive focal length lens so that said focusable beam shaping optics focus both said first laser beam and said second laser beam in an elliptically shaped focal point on said fluid stream.

12. The optical combiner of claim 11 wherein said optical beam combiner is a dichroic beam combining mirror.

13. The optical combiner of claim 11 further comprising:
    a first adjuster that adjusts said negative focal length lens in said beam adjuster in a first direction that is substantially orthogonal to said second laser beam;
    a second adjuster that adjusts said positive focal length lens in said beam adjuster in a second direction that is substantially orthogonal to said second laser beam.

* * * * *